US011974524B2

(12) United States Patent
Ross et al.

(10) Patent No.: US 11,974,524 B2
(45) Date of Patent: *May 7, 2024

(54) MYCELIUM GROWTH BED WITH PERFORATION LAYER AND RELATED METHOD FOR CREATING A UNIFORM SHEET OF MYCELIUM FROM A SOLID-STATE MEDIUM

(71) Applicant: MycoWorks, Inc., Emeryville, CA (US)

(72) Inventors: Philip Ross, San Francisco, CA (US); Matthew L. Scullin, San Francisco, CA (US); Nicholas Wenner, Sebastopol, CA (US); Jordan Chase, Oakland, CA (US); Quinn Miller, Berkeley, CA (US); Ryan Salditos, San Francisco, CA (US); Phil McGaughy, Oakland, CA (US)

(73) Assignee: MycoWorks, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/210,622

(22) Filed: Jun. 15, 2023

(65) Prior Publication Data

US 2023/0320287 A1    Oct. 12, 2023

Related U.S. Application Data

(63) Continuation of application No. 16/657,979, filed on Oct. 18, 2019, now Pat. No. 11,678,617.

(Continued)

(51) Int. Cl.
*A01G 18/22* (2018.01)
*A01G 18/62* (2018.01)
(Continued)

(52) U.S. Cl.
CPC ............ *A01G 18/62* (2018.02); *A01G 18/22* (2018.02); *A01G 18/64* (2018.02); *A01G 18/65* (2018.02);
(Continued)

(58) Field of Classification Search
CPC ........ A01G 18/10; A01G 18/20; A01G 18/22; A01G 18/60; A01G 18/61; A01G 18/62; A01G 18/64; A01G 18/65
(Continued)

(56) References Cited

U.S. PATENT DOCUMENTS 3,842,534 A * 10/1974 Walters ................. A01G 18/62
108/53.5
4,001,966 A * 1/1977 Metzner ................ A01G 18/62
47/1.1
(Continued)

*Primary Examiner* — David J Parsley
(74) *Attorney, Agent, or Firm* — Temmerman Law; Mathew J. Temmerman

(57) ABSTRACT

A mycelium growth bed for growing a solid substrate-bound mycelium through which the mycelium composite is easily and readily removed. This is achieved through the use of a perforation layer embedded between the mycelium substrate and the mycelium composite so as to create a uniform structural weakness and thereby enhancing harvesting abilities of the ex-substrate mycelium via a greatly reduced and uniform tear strength. The perforation layer, through which the mycelium grows, allows for the gated and controlled extrusion of a matrix of colonial cells that may be easily and uniformly delaminated from the underlying mycelium substrate.

12 Claims, 10 Drawing Sheets

Related U.S. Application Data

(60) Provisional application No. 62/747,577, filed on Oct. 18, 2018.

(51) Int. Cl.
*A01G 18/64* (2018.01)
*A01G 18/65* (2018.01)
*C12M 1/12* (2006.01)
*C12N 5/00* (2006.01)

(52) U.S. Cl.
CPC ........... C12M 25/14 (2013.01); C12N 5/0068 (2013.01); *C12N 2533/90* (2013.01)

(58) Field of Classification Search
USPC .......................................................... 47/1.1
See application file for complete search history.

(56) References Cited

U.S. PATENT DOCUMENTS

| | | | | |
|---|---|---|---|---|
| 5,040,328 | A * | 8/1991 | Coon ..................... | A01G 18/62 |
| | | | | 206/505 |
| 6,018,906 | A * | 2/2000 | Pia ......................... | A01G 18/62 |
| | | | | 47/1.1 |
| 6,622,423 | B1 * | 9/2003 | Riccardi ................ | A01G 9/028 |
| | | | | 47/1.1 |
| 11,678,617 | B2 * | 6/2023 | Ross ........................ | C12N 1/14 |
| | | | | 435/395 |
| 2013/0199088 | A1 * | 8/2013 | Juscius .................. | A01G 18/69 |
| | | | | 47/1.1 |
| 2018/0014468 | A1 * | 1/2018 | Ross ........................ | C05F 9/04 |

* cited by examiner

MYCELIUM GROWTH BED WITH PERFORATION LAYER AND RELATED METHOD FOR CREATING A UNIFORM SHEET OF MYCELIUM FROM A SOLID-STATE MEDIUM

RELATED APPLICATIONS

This application is a continuation of U.S. nonprovisional application Ser. No. 16/657,979, filed Oct. 18, 2019 and granted as U.S. Pat. No. 11,678,617 on Jun. 20, 2023, and which claims the benefit of U.S. provisional patent application 62/747,577, filed Oct. 18, 2018, the disclosure of which is incorporated herein in its entirety.

BACKGROUND OF THE DISCLOSURE

Technical Field of the Disclosure

The present embodiment relates generally to methods for creating a mycelium composite, and more particularly, to a method for creating a uniform layer of mycelium composite utilizing a mycelium growth bed having a perforation layer.

Description of the Related Art

Fungal tissue can quickly be amplified to an enormous volume if provided with the appropriate conditions, including proper nutrients available to the organism, gas gradients within the growth environment and humidity, light and temperatures the organism is exposed to as it takes form. Fungi are very sensitive to stimuli in their environment and have the ability to alter the direction and vigor of growth of expanding hyphae in response to gravitropic, thermotropic, thigmotropic, phototropic, chemotrophic, and hydrotropic stimuli. The hyphae of fungi sense and grow around physical impediments that lie in their path of outward expansion. Through the altering of subtle factors, it is possible to prompt and direct fungal hyphae, mycelium and tissue to express a range of variably determined physical characteristics.

A substrate colonized with fungal hyphae, if provided an adequate enclosure and environmental controls, will generate a layer of vegetatively fungal hyphae growing apically from the top of the substrate in a fuzzy and undifferentiated manner using neighbor sensing and searching functions as guidance in their exploration into space beyond sources of nutritional sustenance. Using varying stimuli, this undifferentiated layer of hyphae may be manipulated and formed into a continuous sheet of mycelium biotextile. This sheet of mycelium biotextile, upon harvest, can be cured and finished to take on qualities that are similar in texture, look and performance to plastics, foams and animal skins. Current forms of manufacturing of polymeric materials including animal skins and vinyl create environmental problems in manufacturing and recycling or disposal at the end of a material's utility. The fungal tissue materials and composites described herein may as an alternative to those conventional processes, consist almost entirely of fungal tissues. This fungal material may be used in products which would otherwise be conventionally made using chemical products such as ethylene vinyl acetate foams, polyvinyl chloride plastics, and polyurethane foams, amongst others.

This unusual regime of mycelium growth poses challenges not only in optimizing the growth conditions but also in harvesting such material so as to transform it into an industrially useful material. Treating mycelium that is grown external to its substrate rather than either a mycelium-substrate composite or its fruiting body is neither trivial nor well understood, but necessary for the use of mycelium materials as leather-like textiles. One such method of production involves growing mycelium on rafts in liquid cultures, where cells grow into this raft-matrix from a nutrified soup below. Another such method describes techniques for growing the mycelial cells from a compacted sawdust or wood flower. However, this conventional method has certain downsides that require heavy amounts of post processing for optimizing the mycelium growth conditions and also to transform the harvested mycelium composite into an industrially useful material.

Therefore, there is a need for an efficient and reliable method for creating a uniform layer of mycelium composite with high degree of consistency. Furthermore, such a method would optimize the mycelium growth conditions. Such a method would minimize environmental problems in manufacturing, recycling or the disposal phase of the material. Moreover, such a method would create a mycelium composite in minimal time, cost, and complexity. The present embodiment overcomes shortcomings in the field by accomplishing these critical objectives.

SUMMARY OF THE INVENTION

To minimize the limitations found in the prior art, and to minimize other limitations that will be apparent upon the reading of the specification, the present disclosure provides a method for prompting the growth of gradient-less, consistently textures and planed, uniformly expressed mycelium composite above the solid state mycelium substrate utilizing a mycelium growth bed. The mycelium growth bed comprises a tray having enclosed walls, a lid, and a floor. A conveying platform is configured to fit within the tray and adaptable to support a mycelium substrate thereby forming at least one continuous substrate plane. In the preferred embodiment, a mass of the mycelium substrate is inoculated and colonized with a strain of mycelium composite. The mycelium growth bed further comprises a perforation layer having a plurality of pores and embedded parallel to or coplanar with at least one substrate plane. The perforation layer provides a plurality of initial growth conditions to grow a uniform layer of the mycelium composite that is adaptable to extend through the plurality of pores thereby resulting in a reduction of tear strength within the perforation layer. A porous material is positioned on top of the mycelium substrate and held close to the perforation layer. A lid is detachably attached to the enclosed walls of the tray.

The mycelium substrate is altered for the optimal growth of the pure mycelium sheet or the mycelium composite utilizing at least one altering mechanism. The perforation layer is selected from a group consisting of: a piece of wire mesh, a nylon woven matrix and a fabric. In the preferred embodiment, the uniform layer of mycelium composite extends both through and beyond the perforation layer. The perforation layer connected between the mycelium substrate and the pure mycelium sheet or sheet of mycelium composite reduces the force required to remove a top layer portion of the mycelium composite and/or a sheet of pure mycelium. Further, this reduced amount of force to remove the top layer portion of the mycelium and/or mycelium composite is lower than the delamination force of the mycelium sheet or mycelium composite above the perforation layer. Finally, the inclusion of such a layer leads to increased consistency and increased evenness of surface textures and overall material quality of the mycelium that is removed from above the perforation layer.

The mycelium growth bed easily and readily removes ex-substrate mycelium from the substrate-bound mycelium. Preferably, the perforation layer is embedded between the substrate and the ex-substrate mycelium so as to create a uniform structural weakness and thereby enhancing harvesting abilities of the ex-substrate mycelium via greatly reduced and uniform tear strength. Such a dramatic decrease in the tear strength of an otherwise tough material, mycelium, such as that generated by *Ganoderma Lucidum* or similar, is remarkable, especially when performed along a precise plane. The perforation layer acts as a barrier between a fungal colony, containing its nutritional media (substrate), and a layer or layers of mycelium and/or mycelium composite.

The perforation layer includes a prescribed porosity with an average hole size within the plurality of pores is between 0.1 micron and 1.0 millimeter, whereby mycelium occupies the plurality of the pores resulting in a reduction of tear strength of within this layer to less than 200 N/mm. Furthermore, the perforation layer is a layer that fungal matter will not readily degrade structurally, or one that will degrade in a predictable way and over a prescribed period of time. The perforation layer is connected such that the force needed to remove the top mycelium layer(s) is lower than the delamination force of the mycelium layers and/or mycelium composites above the perforation layer. The preferred method enables the precise control of grown mycelium layers ex-substrate, such as for use as leather-like materials with precise intrasheet thickness uniformity. Further, the perforation layer acts as an intermediary layer through which the mycelium grows, allows for the gated and controlled extrusion of a matrix of colonial cells of fungal mycelium for purposes of continuous manipulation as that matrix is growing.

The preferred embodiment provides a composition and related method for prompting the growth of gradient-less and uniform expression of the mycelium composite above the solid state mycelium substrate. The method commences by providing the mycelium growth bed. Next, the mycelium substrate is altered utilizing at least one altering mechanism. Then, the mycelium substrate is placed on the conveying platform configured to fit within the tray and adaptable to support the mycelium substrate and forming at least one, continuous substrate plane. Next, the perforation layer is embedded along at least one surface or plane of the substrate monolith. The plane can be, but is not limited to; flat, linear, curvilinear, compound, convex, and/or concave. The perforation layer may also comprise multiple "sides" or "faces" of the substrate monolith in order to result in pure mycelium or mycelium composite sheets with complex, three-dimensional geometry. Next, the plurality of initial growth conditions is provided thereby enabling the mycelium composite to grow and extend through the plurality of pores of the perforation layer. Thereafter, the uniform layer of the mycelium composite is obtained. The growth of the mycelium composite is periodically manipulated. Then, the mycelium composite is uniformly separated from the mycelium substrate. The perforation layer creates the delimiting structure for growing additional organismal expressions of mycelium cells.

A first objective of the present invention is to create a monolithic structure of mycelium, a mycelium's nutritional substrate, and a homogenous sheet or assembly of pure mycelium or mycelium composite, wherein all are mechanically contiguous during growth and fermentation, and yet simultaneously easily separated therefrom when the fermentation process is complete.

A second objective of the present invention is to provide a method for prompting the growth of gradient-less and uniform expression of the mycelium composite utilizing a mycelium growth bed.

A third objective of the present invention is to provide a method that easily and uniformly removes a mycelium material from a substrate-bound mycelium.

A fourth objective of the present invention is to provide an efficient and reliable method for creating a uniform layer of mycelium composite with high degree of consistency.

Another objective of the present invention is to provide a method that creates a mycelium composite in minimal time, cost and complexity.

Yet another objective of the present invention is to provide a method that minimizes environmental problems in manufacturing, recycling or disposal phase of the mycelium composite.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about' means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
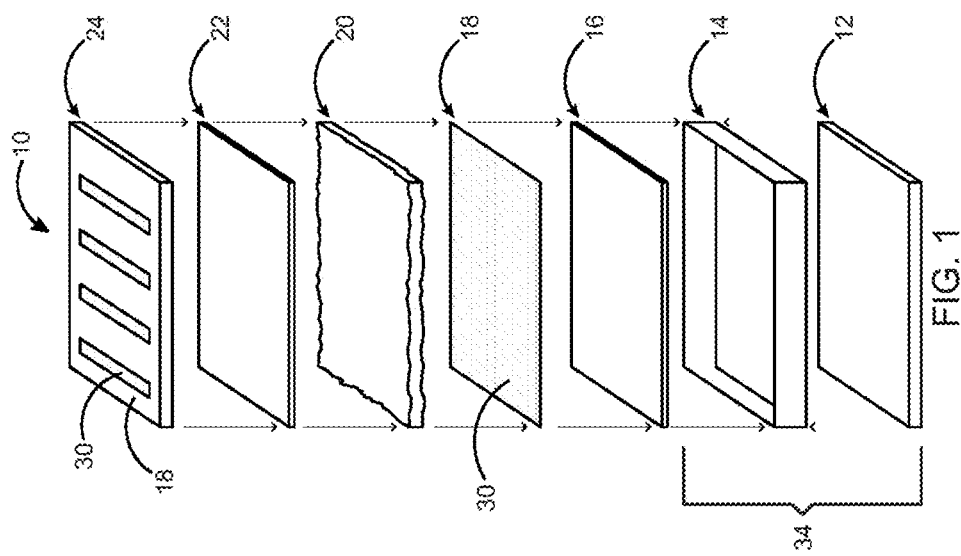
FIG. 1 is an exploded view of a growth bed for creating a uniform layer of mycelium composite according to a preferred embodiment of the present invention.
Figure 2:
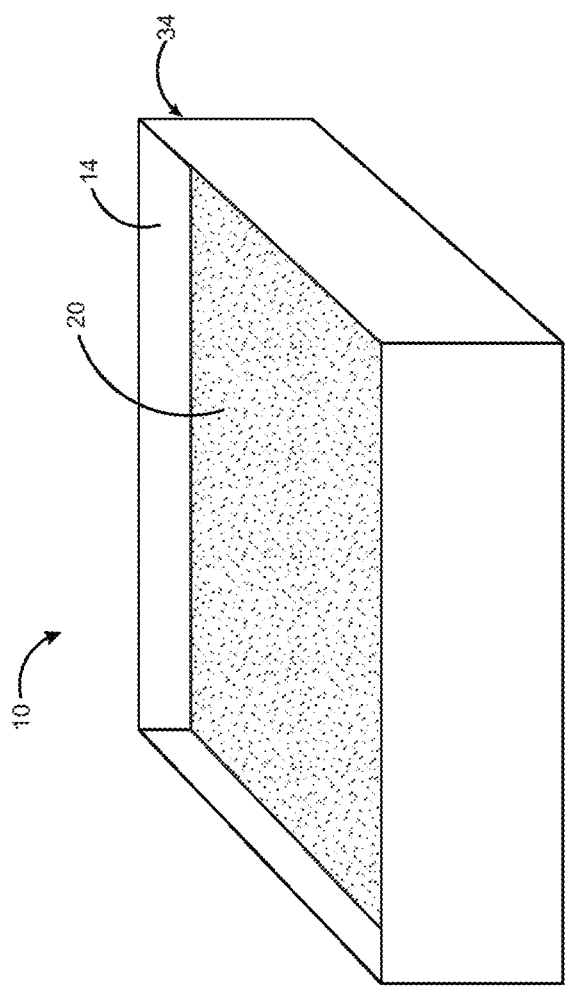
FIG. 2 is a perspective view of the growth bed, illustrating an enclosed wall and a floor of the growth bed according to a preferred embodiment of the present invention.
Figure 3:
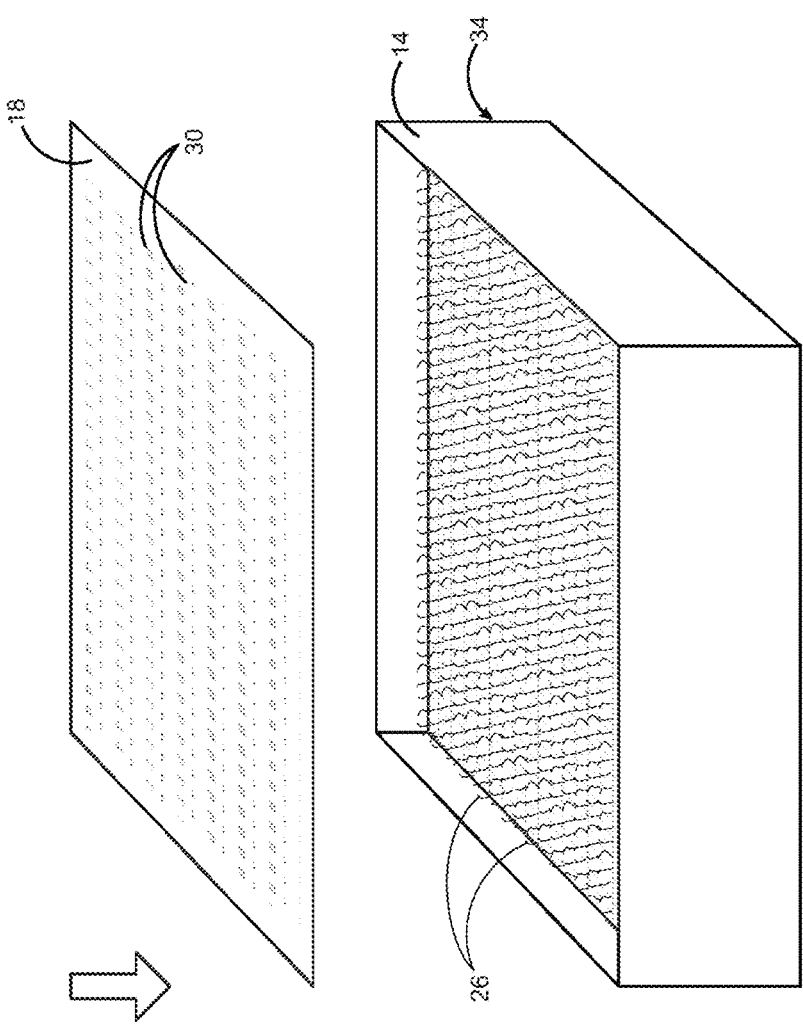
FIG. 3 is an exploded view of the growth bed, illustrating a perforation layer being laid down on top of a solid state mycelium substrate according to a preferred embodiment of the present invention.
Figure 4:
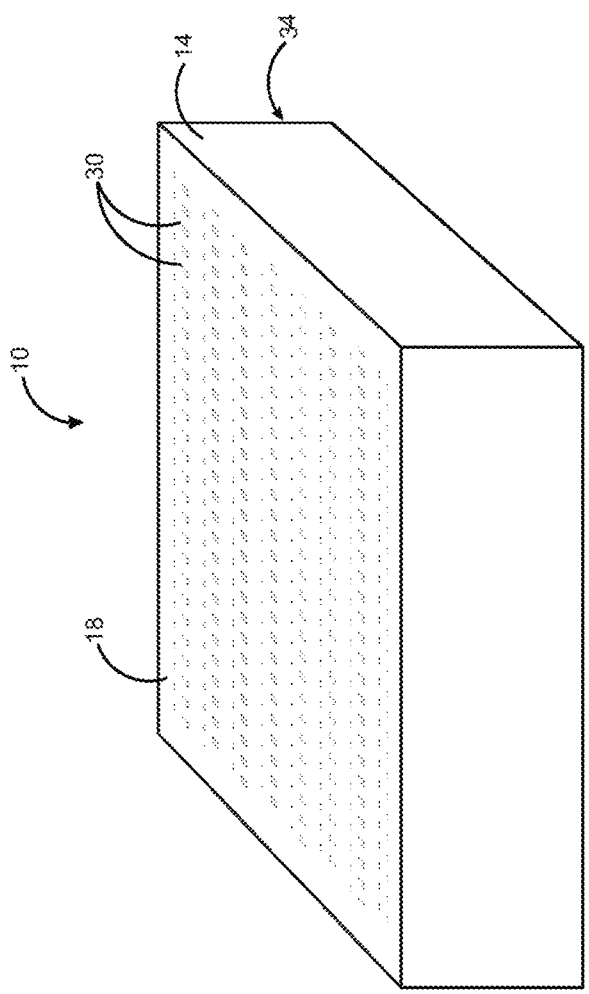
FIG. 4 is a perspective view of the growth bed enclosed with the perforation layer according to a preferred embodiment of the present invention.

The present embodiment is a method for prompting the growth of gradient-less and uniform expression of a mycelium composite 26 (FIG. 5) above a solid state mycelium substrate 20 utilizing a mycelium growth bed 10 as shown in FIG. 1. The mycelium growth bed 10 comprises a tray 34 (see FIG. 4) having an enclosed wall 14 and a floor 12. A conveying platform 16 (see FIG. 1) is configured to fit within the tray 34 and adaptable to support a mycelium substrate 20 thereby forming at least one continuous, and in some embodiments, flat substrate plane. In the preferred embodiment, a mass of the mycelium substrate 20 is inoculated and colonized with a strain of mycelium composite 26. The mycelium growth bed 10 further comprises a perforation layer 18 having a plurality of pores and embedded along the at least one substrate plane. A porous material 22 is positioned on top of the mycelium substrate 20 and held close to the perforation layer 18. A lid 24 is detachably attached to the enclosed wall 14 of the tray 34.

The mycelium substrate 20 is altered for the optimal growth of the mycelium composite 26 utilizing at least one altering mechanism. In this preferred embodiment of the present invention, hardwood or softwood particles may be altered or amended with rye grains or other materials that are rich in nitrogen. The mycelium substrate 20 may be further altered with respect to its pH balance through the addition of calcium carbonate or other calcium sources such that the substrate 20 is adequate for the optimal growth and propagation of the mycelium composite 26. The mycelium substrate 20 may be further prepared with the addition of water such that the hydration of the substrate 20 is saturated to conditions that are adequate for the optimal growth and propagation of mycelium composite 26. In the preferred embodiment, the mycelium substrate 20 is prepared to work in accordance with species that include the *Ganodermas* and *Trametes*, the order Polyporales generally, Schysophyllum, and including all saprobic fungal candidates that derive sustenance from lignin and cellulose-rich sources.

Figure 5:
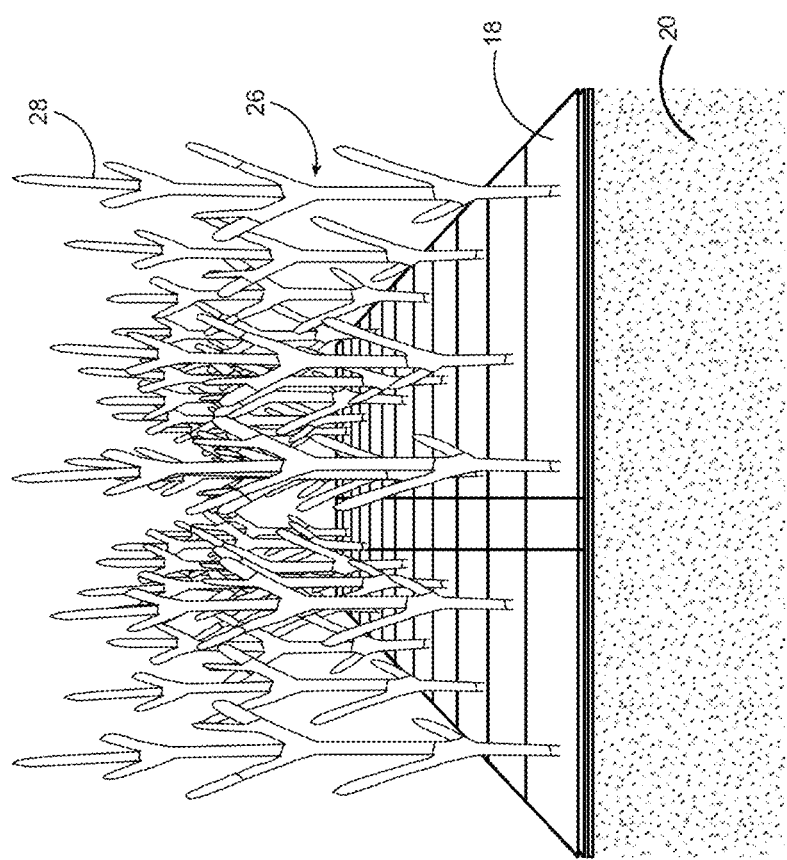
FIG. 5 is a perspective view of the growth bed, illustrating a first layer of mycelium composite grown up through a plurality of pores of the perforation layer according to a preferred embodiment of the present invention.

Preferably, the perforation layer 18 is selected from a group consisting of: a piece of wire mesh, a nylon woven matrix and a fabric. As shown in FIG. 5, a uniform layer of mycelium composite 26 grows within the growth bed 10 utilizing a plurality of initial growth conditions and extends both through and beyond this perforation layer 18 thereby resulting in a reduction of tear strength within the perforation layer 18. The positioning of the perforating layer 18 between the substrate 20 and the ex-substrate mycelium composite 26 creates a uniform structural weakness and thereby enhanced harvesting attributes of the ex-substrate mycelium composite 26 via greatly reduced and uniform tear strength. In one embodiment of the present invention, the perforation layer 18 includes tear strength of less than 200 N/mm. The perforation layer 18 connected between the mycelium substrate 20 and the mycelium composite 26 reduces the force required to remove a top layer portion 28 of the mycelium composite 26. Further, this reduced amount of force to remove the top layer portion 28 (FIG. 5) of the mycelium composite 26 is lower than the delamination force of the mycelium layers and/or mycelium composite 26 above the surface.

Preferably, the perforation layer 18 includes a prescribed porosity with an average hole size within the plurality of pores is between 0.1 micron and 1.0 mm, whereby mycelium composite 26 occupies the plurality of the pores 30 resulting in a reduction of tear strength of within this layer to less than 200 N/mm. An advantageous feature of the perforation layer 18 is that, no fungal matter will readily degrade the structure of this layer 18. The preferred method enables the precise control of grown mycelium layers ex-substrate 26, such as for use as leather-like materials with precise intra-sheet thickness uniformity. Further, the perforation layer 18 acts as an intermediary layer through which the mycelium composite 26 grows and allows for the gated and controlled extrusion of a matrix of colonial cells of fungal mycelium for purposes of continuous manipulation as that matrix is growing.

In another embodiment of the present invention, the method for embedding such a perforation layer 18 is such that the perforation layer 18 is laid along a surface plane of the mycelium substrate 20 during growth such that the mycelium composite 26 is allowed to grow through it and extend beyond it.

In yet another alternative embodiment of the invention, a mesh, fibers, or other material that might act as a permeable membrane for the mycelium composite 26 to grow through is introduced within or upon the plane or planes of the colonized mycelium substrate 20. The mesh or the permeable membrane is made in such a manner as to have a plurality of pores or openings, which can range in size between 0.1 micron and 1 millimeter and should be spaced regularly throughout the surface of the material so as to encourage even and regular growth of the mycelium composite 26 through it. The material that comprises this mesh, fiber, or permeable membrane should be made from nylon or other substances that are resistant to decomposition from physical association with saprobic fungi; or alternatively, predictably degrades over a predetermined period of contact with the organism of choice, such that the material can be considered organic waste when the substrate-mycelium complex is finally discarded.

In use, as shown in FIGS. 1-4, the perforation layer 18 is placed on an exposed surface of the colonized mycelium substrate 20 and is intended to physically isolate the growing fungal material from the substrate 20. It can take the form of a membrane or fabric that is permeable to the growing fungal material but not to the particles of the mycelium substrate 20. Further, the perforation layer 18 enables the fungal material to be cleanly removed without damaging the mycelium substrate 20 during a delamination process.

Preferably, the mycelium growth bed 10 acts as a regulating structure that determines the expression of an organism grown within particular conditions and also as a way to easily delaminate arbuscular expressions of the mycelium composite 26 above a plane or planes of the colonized mycelium substrate 20.

The perforation layer 18 facilitates the uniform separation of the fungal material from the mycelium substrate 20 by controlling the interaction of the substrate 20 with the extruded fungal material. Thus, the perforation or intermediate layer 18 prevents the fungal material from permanently adhering to the mycelium substrate 20 and damaging or tearing of the substrate 20 when removing the fungal material. The mycelium substrate 20 can thus be reused to grow additional mycelial structures. When the living fungal tissue has been removed from the mycelium substrate 20 from which it has grown, the living fungal tissue can be reattached to the same or similar substrates and then allowed to reform as a result of natural bonding and fusing of fungal hyphae. This can be a somatic clonal type or might be differentiated sexually or by different species. The perforation layer 18 may be fully or partially permeable across its surface. Preferably, growth of fungal material will be blocked in impermeable areas thereby allowing for masked or patterned growth.

In the preferred embodiment, the end result of the mycelium growth bed 10 structure and related method is the creation of a matriced gate or delimiting structure by the perforation layer 18 through which vegetatively growing apical fungal cells can readily be expressed thus determining what grows outwards. As a result of mycelium composite 26 growing through the perforation layer 18, the living tissue becomes organized into a uniformized mass across a given area with the perforation layer 18 acting as a non adherable backing upon which reoriented topical mycelia can be deformed against. As the growth occurs, heterogeneities of the mycelium substrate 20 make it through the matriced gate or the delimiting structure. Because the regularized mass of mycelium per unit area, this allows for one to know the force per area and moreover to regularize the force per area, thereby facilitating the mechanical delamination processing step without causing tearing, damage or rough areas; essentially acting as an engineered failure point.

In the preferred embodiment, if intentional inconsistencies are desired within the fungal material, disturbances across the plane of growth may be induced through environmental controls and application of various physical and chemical treatments. In one embodiment, different environmental controls are applied to particular regions of the growing material to create specific desired and localized effects. For example, the relative concentrations of gaseous $O_2$ and $CO_2$ may be used to create desired growth habits. In another instance, control of temperature can be used to similar effect. In another instance, aspirated air applied to areas of the growing surface may be used to prevent or promote certain developments of the growing fungal organism.

Figure 6:
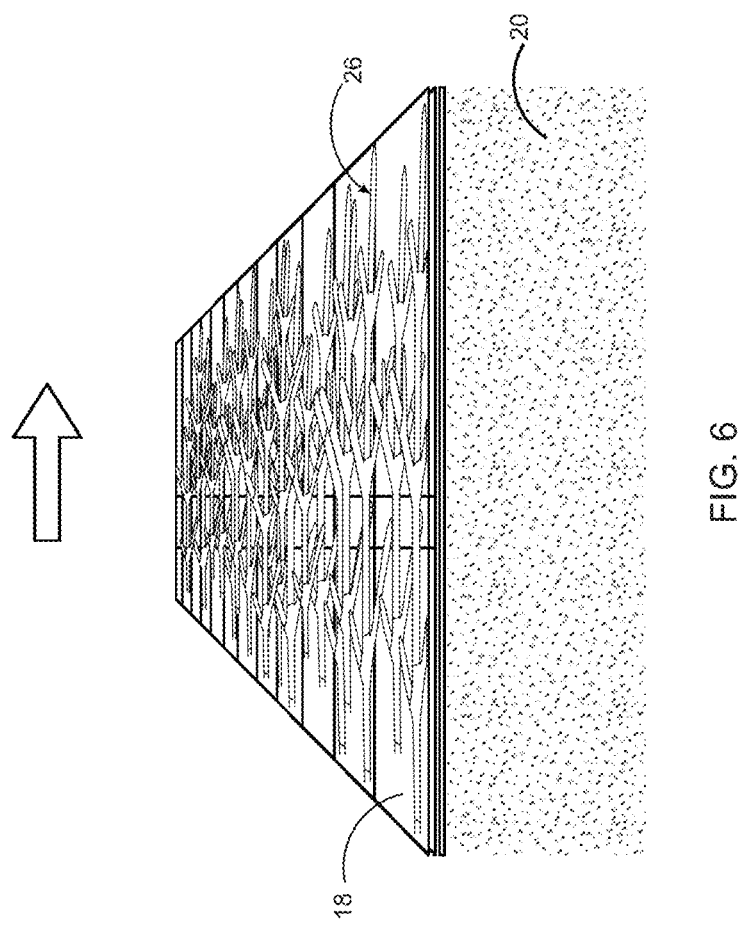
FIG. 6 is a perspective view of the growth bed, illustrating the first layer of mycelium composite being mechanically flattened in a first direction according to a preferred embodiment of the present invention.
Figure 7:
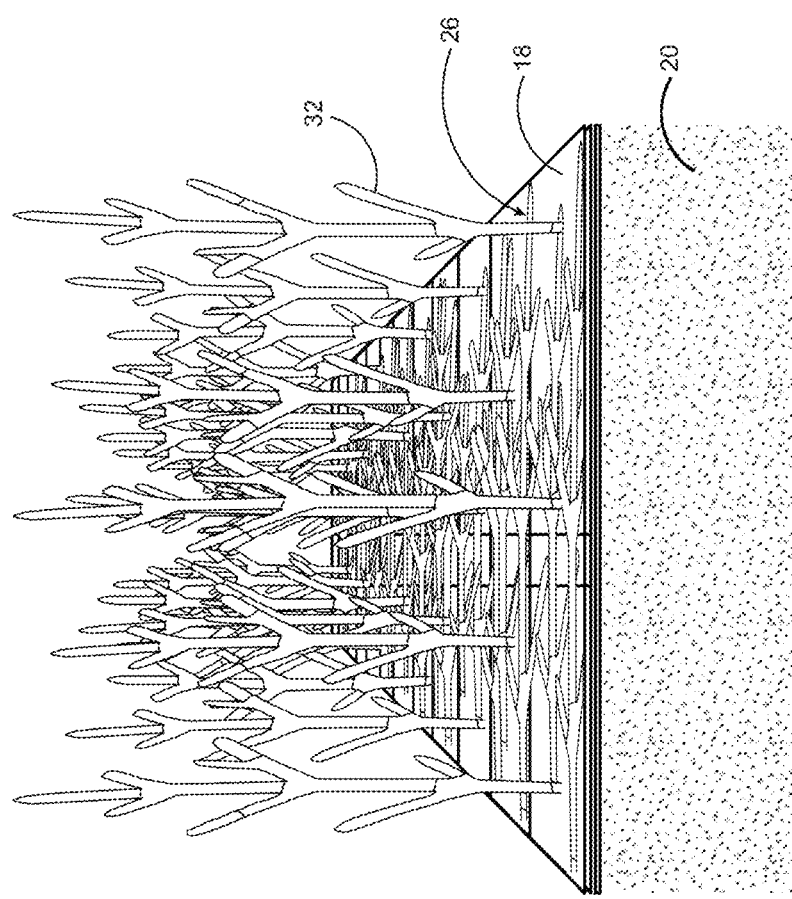
FIG. 7 is a diagrammatic image of the growth bed, illustrating the flattened first layer of mycelium composite and a second layer of mycelium composite grown up through the plurality of pores of the perforation layer according to a preferred embodiment of the present invention.
Figure 8:
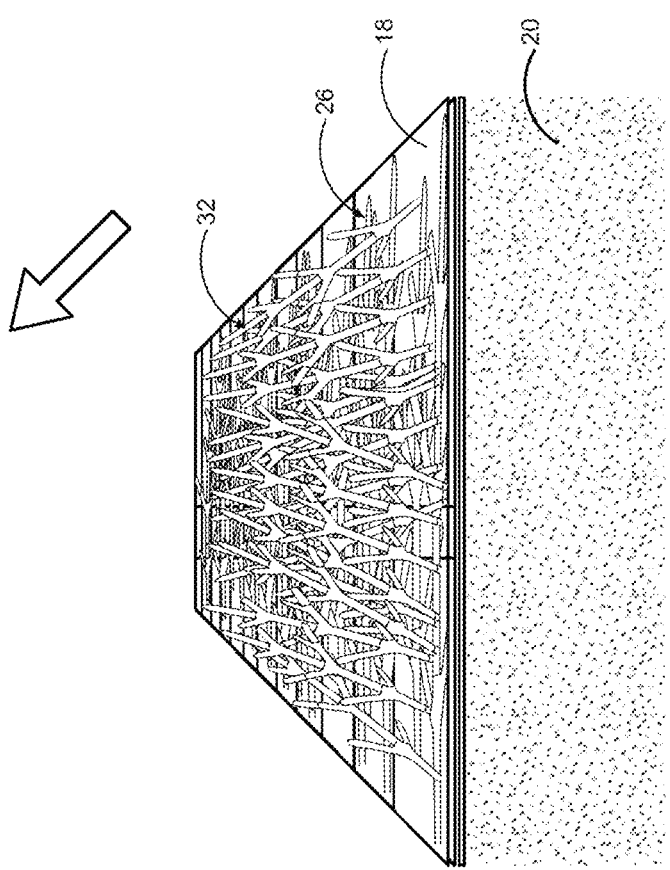
FIG. 8 is a perspective view of the growth bed, illustrating the second layer of mycelium composite being mechanically flattened in a second direction according to a preferred embodiment of the present invention.

In one embodiment of the present invention, the manipulation of fungal materials may be performed by physical means using the perforation layer 18 as a backing between the growing mycelium composite 26 and the mycelium substrate 20. As shown in FIG. 6, a first layer of mycelium composite 26 is mechanically flattened in a first direction and laid in one direction using a roller. The direction in which the first layer is flattened is shown as an arrow in FIG. 6. FIG. 7 illustrates the flattened first layer 26 of mycelium composite and a second layer of mycelium composite 32 grown up through the plurality of pores 30 of the perforation layer 18. FIG. 8 illustrates the second layer of mycelium composite 32 being mechanically flattened in a second direction as shown by an arrow. The roller depresses the hyphae into a planar form. When the hyphae regrow, they express an arbuscular form and the rolling method is used to weave the body of the fungal material into novel patterns. Due to such physical manipulation of the fungal material, the hyphae can be grown into particular and determined directions such that they may be arranged into orthogonal structures, lattices, and other two-dimensional and three-dimensional organizations. With the consistent and patterned manipulations of hyphal growth resulting from this method, the fungal material can be formed in layered structures with determined arrangements of fungal tissue (e.g. alternating layers with orthogonally-arranged fibers). In addition to determining the structure of the hyphal network, this form of manipulation also homogenizes the mycelial tissue by deterring it from differentiating and developing primordia or other tissues.

In another embodiment of the present invention, in order to direct growth and/or produce composite materials, materials may be incorporated into the growing fungal tissue while the fungal material is still viable. In one embodiment, cellulose-based, synthetic or other organic fibers including various textile forms (e.g. woven, knit, fulled, felted) of preferred lengths and structural characteristics are deposited on the exposed surface of the growing fungal tissue thereby allowing for the growth of a composite material. The composition and organization of the composite fibers enables the fungal tissue to be engineered thereby enhancing mechanical properties of the overall material including tensile and compressive strength.

In yet another embodiment of the present invention, the fungal tissue can be grown through 2D and 3D matrices and objects of various materials to create composites with desired characteristics and qualities. This added material may be composed of any material that fungal cells can grow through (pore size larger than 0.1 micron). These materials may be pressed onto or near the surface of the growing cells above the perforation layer 18 or otherwise impressed upon its surface or placed between two or more layers of growing fungal material such that these materials are then incorporated into the fungal tissue.

Creating and working with layers of mycelial cells is facilitated by the solid backing that the perforation layer 18 provides. Since suitable pressure to fold over a layer of mycelial cells would not be possible in a system wherein the cells grew over a gelatin or liquid nutrient soup such mechanical processing is possible in the present invention because the solid gate prevents a backing against which mechanical pressure may be applied. The process of mechanical folding against a solid backing is shown through FIGS. 5-8. The folding of layers increases cross linking (within, amidst and between cells) which helps to increase the sheer strength of the resultant material comprises pure mycelium or mycelium composite.

In one embodiment of the present invention, modifications of the growing mycelium substrate 20 might be made to achieve similar growth parameters in expression without an intermediary non-reactive layer. Instead of a permeable physical material like nylon, a screen print or application of antibiotic substance may be applied to the substrates surface to achieve a similar outcome of determined expression or non-expression of mycelium at a particular X,Y coordinate of the growing substrate's surface. Similarly, a laser or other heating element, or a waterjet may be used to sinter (abrade, cut, kill, or otherwise alter) the surface of the living substrate to achieve the same permeable capabilities of the nylon.

In another embodiment of the invention, a porous material including but not limited to a cotton fabric is introduced on top of the growing mycelium substrate. Held taught in such a way that it comes in close physical contact to the underlying nylon or other material that had previously been introduced to the living substrate. While nylon and cotton have the greatest variability, other meshes may be used, such as electronic meshes, Kevlar® or other specialized materials may be incorporated directly within a growing mycelium composite.

In another alternative embodiment of the invention the entire growth bed is inverted (turned substantially upside down) at least once during the growing process.

In still further embodiments the layer may be considered an interfacial layer that is a barrier between a fungal colony containing its nutritional media (substrate) and a layer or layers of mycelium and/or mycelium composite. The interfacial layer reduces the force needed to remove the top mycelium layer(s) such that it is lower than the delamination force of the mycelium layers and/or mycelium composite above the interface.

In yet another embodiment, the growth and direction of mycelium composite 26 may be influenced through remote action such as sound or vibration are other alternatives. Elements that include thigmotropic influences, sonic waves or other signals, lasers, or vibrating air that causes the movement of the mycelium composite 26 to come in contact with itself as a result. In another alternative embodiment, a magnetic device underneath, linking to a ball or other metal object inside the vessel which rolls and moves around the surface to accomplish the functions required for tending the growing mycelium may be employed.

Figure 9:
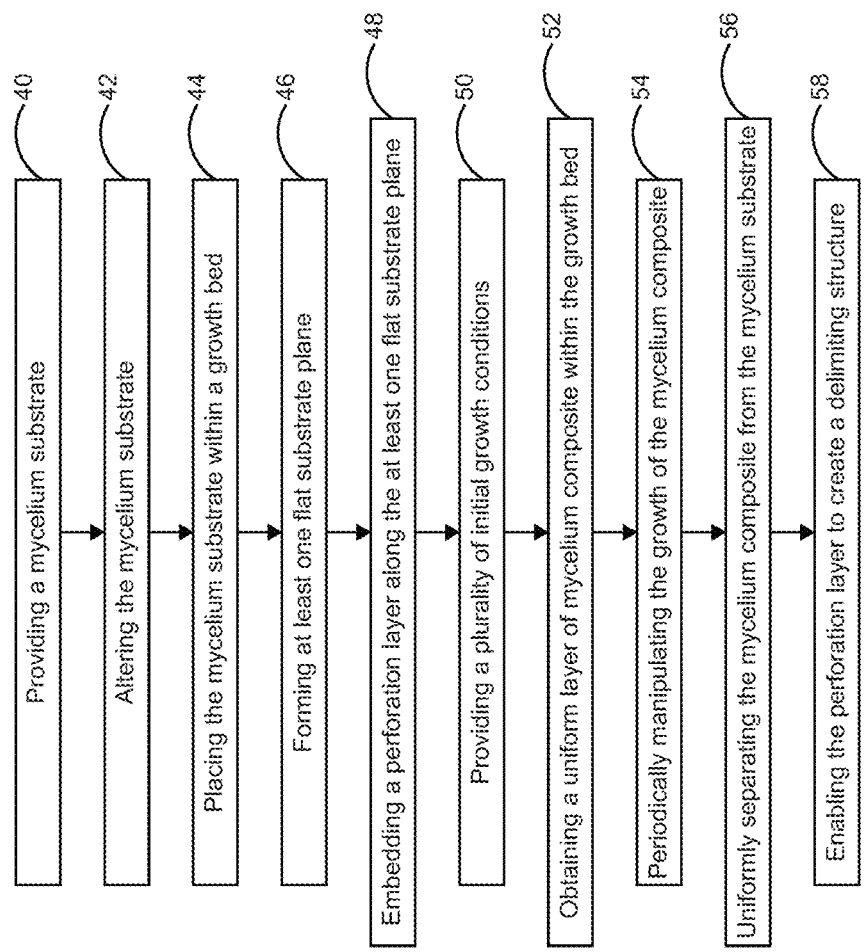
FIG. 9 is a flowchart of a method for prompting the growth of gradient-less and uniform expression of the mycelium composite above the solid state mycelium substrate.

FIG. 9 is a flowchart of a method for prompting the growth of gradient-less and uniform expression of the mycelium or mycelium composite above the solid state mycelium substrate. The method commences by providing the mycelium growth bed as shown in block 40. Next, the mycelium substrate is altered utilizing the at least one altering mechanism as shown in block 42. Then, the mycelium substrate is placed on the conveying platform configured to fit within the tray and adaptable to support the mycelium substrate as shown in block 44 and forming the at least one substrate plane as shown in block 46. Thereafter, the perforation layer is embedded along the at least one substrate plane as shown in block 48. Next, the plurality of initial growth conditions is provided thereby enabling the mycelium composite to grow and extend through the plurality of pores of the perforation layer as shown in block 50. The uniform layer of the mycelium composite is obtained as indicated at block 52. The growth of the mycelium composite is periodically manipulated as indicated at block 54. Next, the mycelium composite is uniformly separated from the mycelium substrate as shown in block 56. The perforation layer creates the delimiting structure for growing additional organismal expressions of mycelium cells as shown in block 58.

Figure 10:
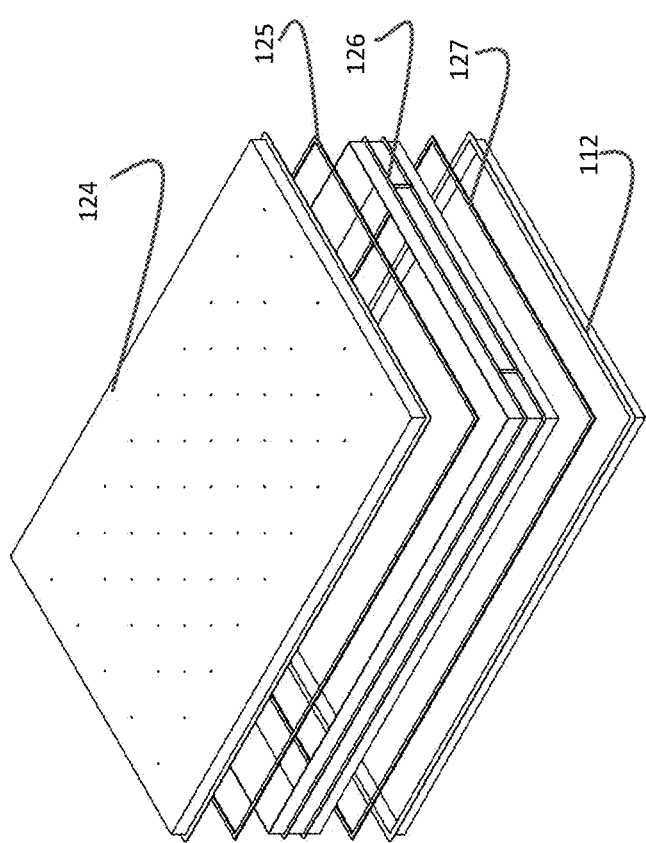
FIG. 10 is a perspective view of an alternative embodiment of the invention.

In an alternative embodiment of the invention shown in FIG. 10, the system comprises a top lid 124, a first seal 125, walls 126, a second seal 127, and a floor 112, in addition to some of all of the additional components previously described.

Modifications of the growing substrate may be made to achieve similar growth parameters in expression without an intermediary non-reactive layer. While a permeable physical material such as but not limited to cotton, linen, polyester, rayon, metal mesh, plastics such as latex with induced pores, nylon, cashmere wool, Kevlar®, silk, satin, or a screen print may be used, a similar outcome of determined expression or non-expression of mycelium at a particular X,Y coordinate of the growing substrate's surface can be accomplished through application of an antibiotic substance applied to the substrates surface. Similarly, a laser or other heating element can be used to sinter the surface of the living substrate to achieve the same permeable capabilities of the nylon.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A mycelium growth bed comprising:
   a tray having an enclosed wall and a floor;
   a mycelium substrate that being inoculated and colonized with a strain of mycelium composite, the mycelium substrate being altered for the optimal growth of mycelium composite utilizing at least one altering mechanism;
   a conveying platform configured to fit within the tray and adaptable to support the altered mycelium substrate thereby forming at least one continuous substrate plane;
   a porous material positioned on top of the mycelium substrate; and
   a lid;
   whereby the porous material optimizes the growth of at least one uniform sheet of mycelium composite adaptable to extend through the plurality of pores creates a uniform structural weakness and thereby resulting in an area of reduced tear strength, the reduced tear strength area decreasing the force required to remove a top layer portion of the mycelium composite; and
   wherein the altering mechanism is calcium carbonate.

2. The mycelium growth bed of claim 1 wherein the at least one uniform sheet of mycelium composite grows through the plurality of pores utilizing a plurality of initial growth conditions.

3. The mycelium growth bed of claim 1 wherein the growth of the mycelium composite is periodically manipulated to obtain the mycelium composite in desired characteristics.

4. The mycelium growth bed of claim 1 wherein the lid is adaptable to detachably attach with the enclosed wall of the tray.

5. A mycelium growth bed comprising:
a tray having an enclosed wall and a floor;
a conveying platform configured to fit within the tray and adaptable to support a mycelium substrate thereby forming at least one continuous substrate plane, the mycelium substrate being inoculated and colonized with a strain of mycelium composite, the mycelium substrate being altered for the optimal growth of mycelium composite utilizing at least one altering mechanism;
enabling the growth of a uniform sheet of mycelium composite within the tray, the one uniform sheet of mycelium composite adaptable to extend through the plurality of pores thereby resulting in a reduction of tear strength within the layer;
a porous material positioned on top of the mycelium substrate and held close to the layer; and
a lid adaptable to detachably attach with the enclosed wall of the tray;
whereby the positioning of the layer between the substrate and the mycelium composite creates a uniform structural weakness and reduces the tear strength within the layer thereby decreasing the force required to remove a top layer portion of the mycelium composite; and
wherein the altering mechanism is calcium carbonate.

6. The mycelium growth bed of claim 5 wherein the layer uniformly separates the mycelium composite from the mycelium substrate during a delamination process without damaging the mycelium substrate.

7. The mycelium growth bed of claim 5 wherein the layer is selected from a group consisting of: a piece of wire mesh, a nylon woven matrix and a fabric.

8. The mycelium growth bed of claim 5 wherein the layer exhibits a tear strength of under 200 N/mm.

9. A method for prompting the growth of gradient-less and uniform expression of a mycelium composite above a solid-state mycelium substrate, the method comprising the steps of:
a) providing a mycelium growth bed having a tray, a conveying platform, a layer, a porous material and a lid;
b) altering the mycelium substrate utilizing at least one altering mechanism;
c) placing the mycelium substrate on the conveying platform configured to fit within the tray and adaptable to support the mycelium substrate thereby forming at least one continuous substrate plane, the mycelium substrate being inoculated and colonized with a strain of mycelium composite;
d) embedding the layer along the at least one continuous substrate plane;
e) growing a uniform sheet of mycelium composite through a plurality of pores of the layer thereby resulting in a reduction of tear strength within the layer;
f) obtaining a uniform sheet of mycelium composite within the growth bed;
g) periodically manipulating the growth of the mycelium composite to obtain the mycelium composite in desired characteristics;
h) uniformly separating the mycelium composite from the mycelium substrate; and
i) enabling the layer to create a delimiting structure for growing additional organismal expressions of mycelium cells.

10. The method of claim 9 wherein the layer exhibits a tear strength of under 200 N/mm.

11. The method of claim 9 wherein the layer uniformly separates the uniform sheet of mycelium composite from the mycelium substrate during a delamination process.

12. The method of claim 9 wherein the layer prevents the mycelium composite from permanently adhering to the mycelium substrate and damaging the substrate while separating the mycelium composite from the mycelium substrate thereby enabling the substrate to be reused to grow additional mycelial structures.

* * * * *